Figure 1:
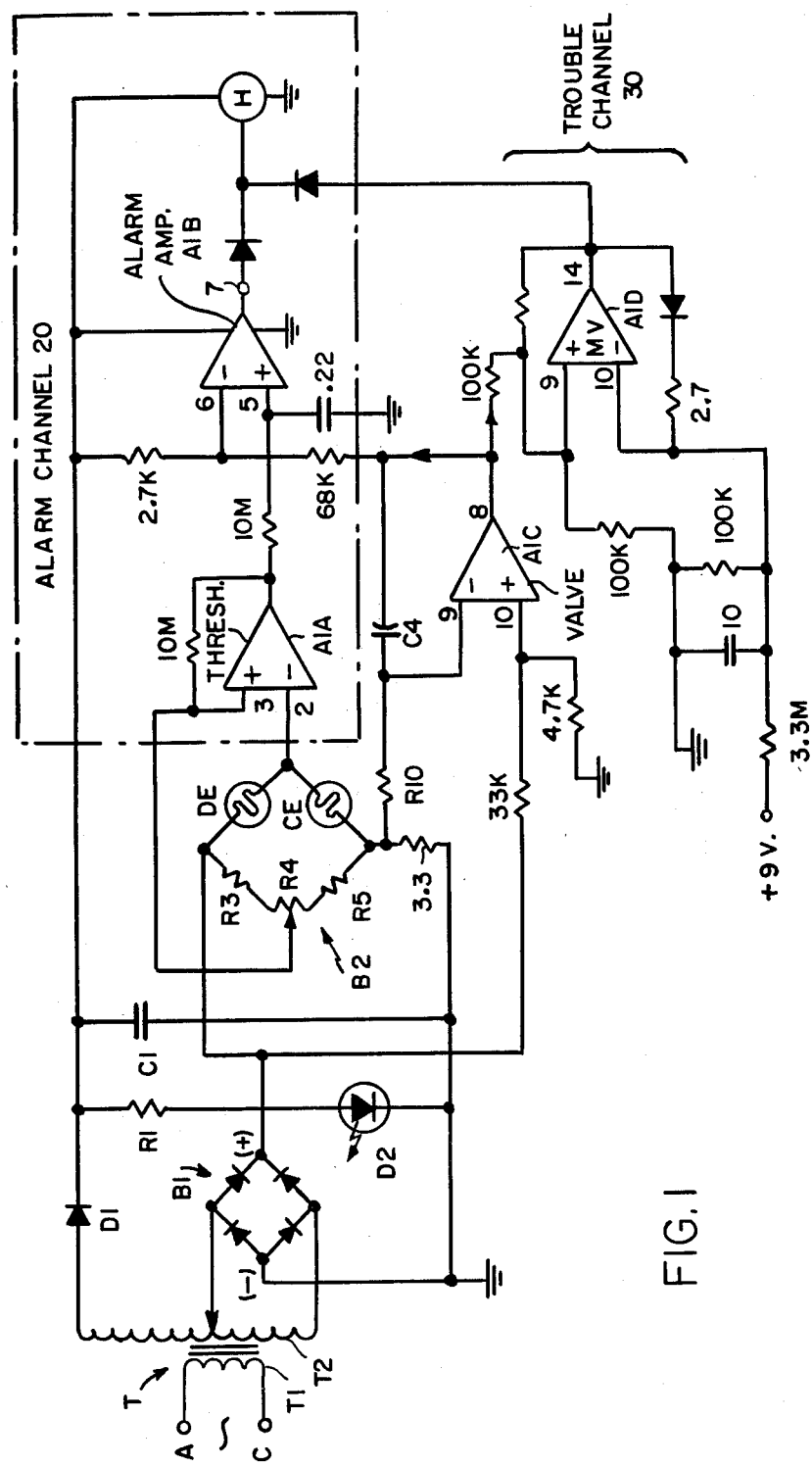

United States Patent [19]

Enemark

[11] 4,219,806
[45] Aug. 26, 1980

[54] DUAL ALARM GAS DETECTOR

[75] Inventor: Robert B. Enemark, Duxbury, Mass.

[73] Assignee: American District Telegraph Company, Jersey City, N.J.

[21] Appl. No.: 942,880

[22] Filed: Sep. 15, 1978

[51] Int. Cl.² .............................................. G08B 17/10
[52] U.S. Cl. .................................. 340/632; 73/27 R; 422/96
[58] Field of Search ....................... 340/632, 633, 634; 73/23, 27 R; 23/232 E; 422/96, 97

[56] References Cited

U.S. PATENT DOCUMENTS

| 3,801,972 | 4/1974 | Hokim et al. | 340/628 X |
| 3,955,186 | 5/1976 | Green et al. | 340/634 X |
| 3,961,400 | 6/1976 | Gintelia et al. | 422/96 |
| 4,007,456 | 2/1977 | Paige et al. | 340/693 X |

Primary Examiner—John W. Caldwell, Sr.
Assistant Examiner—Daniel Myer
Attorney, Agent, or Firm—James H. Grover

[57] ABSTRACT

A detector of a significant gas condition in the atmosphere comprises one or more elements for sensing the condition, the elements being connected to an alarm channel which sounds a warning alarm or controls a corrective device such as a gas valve in the event of an excessive atmospheric condition. The detector includes a threshold sensing and alarm amplifying channel, and a trouble sensing electronic valve or stage responsive to failure of one of the sensing elements both to enable operation of a trouble channel to cause the alarm to indicate the failure and also to inhibit operation of the alarm channel. The trouble channel may also relay power supply failures such as a decrease in battery voltage.

4 Claims, 2 Drawing Figures

4,219,806

DUAL ALARM GAS DETECTOR

BACKGROUND OF THE INVENTION

For detecting the presence of excessive or dangerous fuel gases in the atmosphere of a house, mobile home or industrial plant use has been made of a catalytic, resistive gas sensing element, for example, a wire coated with platinum black. Electrical current supplied to the element heats the element to a temperature at which it will oxidize fuel, e.g. propane or butane, leaking into the atmosphere. Oxidizing the fuel further heats the wire causing an increase in its resistance, which increase can be detected in various ways. One way of detecting the resistance change is by connection of the catalytically coated element in a Wheatstone bridge together with a similar compensating resistive wire element which is uncoated and hence unresponsive to fuel gas. Upon sensing an excessive amount of gas the detector can cause an alarm to be sounded and a gas valve to be closed.

One difficulty with such gas detectors arises if the coated sensing element or compensating element burns open, or a battery power supply weakens. A false alarm resulting from such failures may result or the premise may be left unprotected.

It is an object of the present invention to provide a detector which generates a trouble signal in the event of failure while preventing false alarming. A further object is to signal weakening of the power supply without affecting capability of the detector to alarm. A still further object is to energize a gas cut-off valve only once for each incidence of alarm.

SUMMARY OF THE INVENTION

According to the invention apparatus comprises a resistive element for sensing atmospheric condition; an alarm channel responsive to the element for activating an alarm; an electronic valve responsive to failure of the sensing element; and a trouble channel activated upon response of the valve to actuate the alarm; the valve being coupled both to the alarm channel and trouble channel to enable operation of the trouble channel upon failure of the sensing element and simultaneously to inhibit operation of the alarm channel.

DRAWINGS

Figure 2:
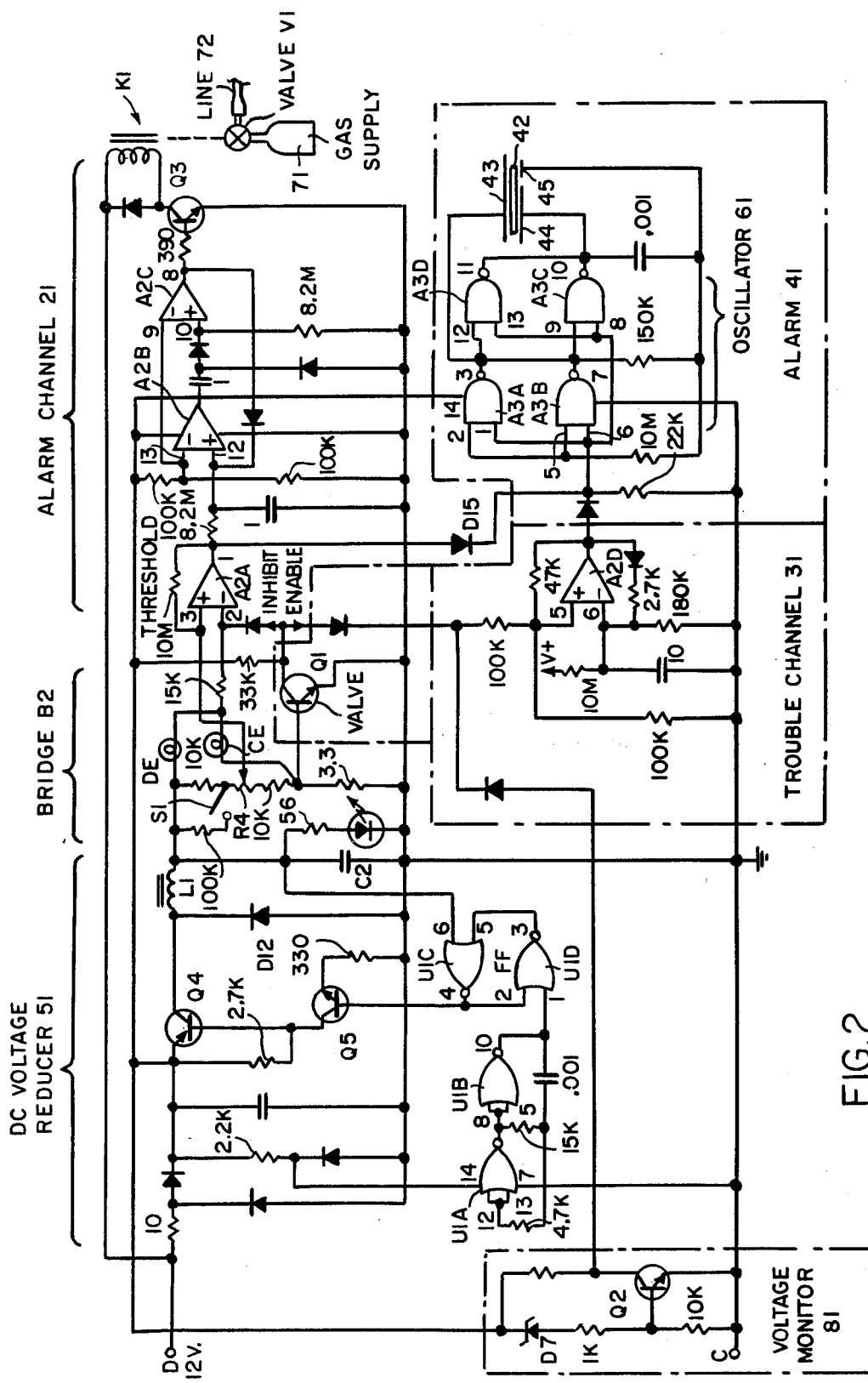

FIG. 1 is a schematic diagram of one form of gas detector according to the invention; and FIG. 2 is a schematic diagram of another form of the invention.

DESCRIPTION

An alternating current powered propane or butane gas detector shown in FIG. 1 uses a catalytic coated wire DE as a gas sensing element. The sensing element DE is connected in a Wheatstone bridge B2 with a compensating, uncoated wire element CE in an adjacent arm on one side of the bridge. Two 10 kilohm resistors R3 and R5 and a 500 ohm potentiometer R4 are connected on the other side. Power for the bridge B2 is supplied from a transformer T1 whose primary winding has input terminals A and C for 115 volt alternating current. One secondary winding T2 applies an AC voltage stepped down to 5 volts to a rectifier bridge B1. The rectifier bridge B1 supplies full wave rectified direct current to the Wheatstone bridge. Another secondary T3 supplies halfwave rectified direct current at about 10 volts through a diode D1 to a solid state lamp D2 indicating a power-on condition, and to an alarm signal amplifier A1B. When fuel gas is sensed by heating of the catalytically coated element DE increased resistance of the coated element drives the bridge toward imbalance, the imbalance voltage being applied to the inputs 2 and 3 of an operational A1A which is one stage of a type LM324 quadruple operational amplifier integrated circuit. This stage A1A constitutes a threshold amplifier which produces an alarm signal at its output 1 when a gas concentration predetermined by the setting of the bridge potentiometer R4 is reached. The alarm signal is applied to the positive input 5 of a second operational amplifier whose output 7 triggers a horn H to sound an alarm so long as the predetermined gas condition persists. The threshold and alarm amplifiers A1A and A1B and the horn H constitute an alarm channel.

Another operational amplifier stage A1D constitutes a trouble channel 30 activated by a two function switch or electronic valve A1C which is also an operational amplifier stage. Normally the valve is held by bias at its positive and negative inputs 10 and 9 so as to have a low or no voltage at its output 8. If the catalytically coated gas sensing element DE should fail by burning open, the negative input 2 of the threshold amplifier A1A would drop toward ground voltage causing an alarm signal at its output 1. However, opening of the element DE would cause a drop in the voltage applied from the grounded junction of the bridge through a 3.9 kilohm resistor R10 to the negative input 9 of the valve A1C. The resulting high voltage at the output 8 of the valve is then applied both to the negative input 6 of the alarm amplifier A1B and to the positive input 12 of the trouble channel stage A1D. The first consequence is that the high positive voltage at the alarm amplifier negative input 6 inhibits the alarm amplifier A1B from applying the alarm signal to the horn H. The second consequence is that the trouble stage A1D which is connected as an asymmetrical multivibrator is caused to oscillate at a frequency of about ½ hertz at which frequency the horn is caused to sound intermittently by pulses at the output of the trouble multivibrator A1D. The two function valve A1C thus simultaneously activates the trouble signal and inhibits the alarm channel from sounding a false alarm caused by the sensing element failure. The intermittent trouble alarm is also caused if the compensating element CE burns open.

In FIG. 2 the gas sensing bridge B2 includes the catalytically coated sensing element DE and compensating element CE of FIG. 1. The bridge is powered by a voltage reducer 51 which steps down the 12 volts at direct current terminals D,C as is standardly supplied in a mobile home, for example, which also has a bottled gas supply 71, connected to a supply line 72 through a valve V1 operated manually or by a solenoid K1.

The purpose of the voltage reducer 51 is to reduce power consumed by the resistive elements in the sensing bridge B2. Direct current is intermittently passed from the DC terminals to an inductive-capacitative network L1-C2 by a control transistor Q4 (2N2907). The 400 millihenry inductance of the ferrite core choke L1 reduces the voltage from 12 volts to about 2 volts without dissipating energy as a resistive voltage divider would. An oscillator comprising two stages U1A and U1B of a quadruple nor-gate integrated circuit, Motorola type MC 14001 BCP generates a 26 kilohertz signal applied to two additional nor-gate stages U1C and U1D connected as a set-reset flip-flop set by the oscillator and reset by voltage swings at the junction of the inductance L1 and capacitance C2. The voltage excursions of the flip-flop are applied through a buffer transistor Q5 (D238H2) to the control transistor Q4 such that energy is stored in the inductance L1 and released at lower than supply voltage but at correspondingly higher amperage taking into account the high, but less than perfect, efficiency of the inductance.

The reduced voltage is applied at two points in the bridge and the imbalance voltage is applied to the positive and negative inputs 3 and 2 of a threshold amplifier A2A constituting one stage of a quadruple operational amplifier, type LM324. The threshold amplifier alarm signal output is applied through a type 1N4454 diode D15 to an alarm circuit 41 constituting a first alarm channel, and also through two alarm amplifiers A2B and A2C of a second alarm channel 21 to the gas valve solenoid K1.

The alarm amplifiers A2B and A2C are connected as a one cycle multivibrator whose single pulse interval is 10 to 15 seconds. This interval is adequate to allow the solenoid K1 to close the gas valve. But being a one cycle multivibrator energizes the solenoid but once each time an alarm condition arises and does not unnecessarily and wastefully maintain activation of the solenoid after it has once closed the gas valve.

The alarm 41 comprises four stages of a Motorola type MC 14011 BCP quadruple nand-gate integrated circuit connected as a 2.9 kilohertz oscillator. The oscillator drives a piezoelectric audible alarm including a piezoelectric crystal 42 with a resonant base electrode 43, a primary electrode 44 and a feedback electrode 45. The base and primary electrodes are connected in the driving circuit for the crystal, while the feedback electrode is connected through a feedback lead to the oscillator. An alarm signal from the threshold amplifier output enables continuous oscillation of the alarm 41.

As in FIG. 1 the circuit of FIG. 2 includes an electronic valve or switch Q1 which normally has no output but which responds to a failure of the catalytically coated sensing element DE by applying an inhibit signal to the threshold detector A2A preventing shutoff of the gas supply when an alarm condition does not exist, but also applying an enable signal to a fourth operational amplifier stage A2D connected as a free running multivibrator having a pulse frequency of ⅓ hertz. When enabled by the valve Q1 the multivibrator A2D modulates the alarm oscillator 61 so that the piezoelectric alarm sounds intermittently rather than continuously as in the case of a true alarm.

The alarm will also sound intermittently in the event that the voltage at the battery terminals DC drops toward an inadequate value. For this purpose a voltage monitor circuit 81 includes a type 1N5237B zener diode D7 in series with 1 kilohm and 10 kilohm resistor across the DC busses. A type 2N3414 transistor Q2 is normally held non-conducting by the voltage drop across the 10 kilohm resistor. When the voltage across the DC busses drops excessively the resultant voltage drop at the base of the monitor transistor Q2 causes the transistor to cease conducting and apply a trouble signal to the trouble stage A2D which in turn causes the alarm 41 to sound intermittently giving warning of a weakening battery or a voltage condition. The direct connection of the voltage monitor 81 to the trouble channel 31 produces the intermittent trouble alarm without disabling the alarm channel from sounding a continuous, true alarm in the event of an excessive gas condition.

It should be understood that the present disclosure is for the purpose of illustration only and that this invention includes all modifications and equivalents which fall within the scope of the appended claims.

I claim:

1. Apparatus for detecting an atmospheric alarm condition comprising:
    a resistive element for sensing atmospheric condition;
    an alarm channel responsive to the element for activating an alarm;
    an electronic valve responsive to failure of the sensing element;
    a trouble channel activated upon response of the valve to actuate the alarm;
    a power supply; and
    means for monitoring the power applied from the supply to the sensing element
    the valve being coupled both to the alarm channel and trouble channel to enable operation of the trouble channel upon failure of the sensing element and simultaneously to inhibit operation of the alarm channel, and the monitoring means having a separate connection to the trouble channel only so as to activate the trouble channel without inhibiting the alarm channel.

2. Apparatus according to claim 1 wherein the alarm channel includes a one cycle multivibrator and a mechanical gas valve electrically energized by the multivibrator and deenergized thereby after time sufficient to close the gas valve upon sensing of an alarm condition.

3. Apparatus according to claim 1 including a resistance bridge, direct current power input terminals, an oscillator powered from the terminals, and a voltage reducer with inductive and capacitative components coupling the oscillator to the bridge whereby to reduce the voltage applied to the bridge.

4. Apparatus according to claim 3 wherein the voltage reducer includes an inductance and a capacitance connected across the power input terminals, the inductive voltage reducer component being connected to the sensing element.

* * * * *